United States Patent [19]

Jordan

[11] 4,018,875
[45] Apr. 19, 1977

[54] AMMONIUM OXALATE PROCESS

[76] Inventor: Robert Kenneth Jordan, The Carlton House, Suite 1431, 550 Grant St., Pittsburgh, Pa. 15219

[22] Filed: Mar. 4, 1975

[21] Appl. No.: 555,151

[52] U.S. Cl. .......................... 423/419 R; 260/538; 123/430

[51] Int. Cl.² .................. C07C 55/06; C01F 5/24; C01B 31/24

[58] Field of Search .......... 260/538, 527 R, 526 R; 423/419–422, 430

[56] References Cited

UNITED STATES PATENTS 1,687,480  10/1928  Buchanan et al. ................. 260/538

FOREIGN PATENTS OR APPLICATIONS 517,455   1/1940   United Kingdom ............... 260/538
477,230  12/1937   United Kingdom ............... 260/538

OTHER PUBLICATIONS

Sienko et al., *Chemistry* 2nd Edition, 1957, McGraw Hill Book Co., NY, NY, p. 496.
*Hackh's Chemical Dictionary*, Edited by Julius Grant, The Blakiston Company, New York, N.Y. 1953, pp. 31 and 46.
Alien Property Custodian (APC), No. 227107, published Apr. 20, 1943, Suzuki, H.

*Primary Examiner*—O. R. Vertiz
*Assistant Examiner*—Gary P. Straub

[57] ABSTRACT

A process for the production of ammonium oxalate and a metal carbonate from a metal oxalate and ammonium carbonate in aqueous or methanol media, ideally using excess ammonium hydroxide.

5 Claims, No Drawings

AMMONIUM OXALATE PROCESS

This invention relates to a process for the production of a solution of ammonium oxalate from metal oxalates and ammonium carbonate.

Ammonium oxalate is not itself a widely used chemical, mainly because oxalates as now produced are expensive. But cheap ammonium oxalate would have an instant market as an intermediate to oxamide, a superior controlled release nitrogenous fertilizer. It is well known in the art to dehydrate ammonium oxalate to oxamide, an example of said art is U.S. Pat. No. 2,646,448 to Joffe which teaches the dehydration of ammonium oxalate over phosphoric acid and ammonium phosphate catalysts to oxamide, but again there have not been any processes available for the economic production of ammonium oxalate on a large scale.

The present commercial process for oxalic acid and other oxalate compounds is based on the carbonylation of caustic soda with carbon monoxide to an aqueous solution of sodium formate which is dehydrated to solid formate, melted carefully at about 260° C and then rapidly fused at 400° C for 5 to 10 minutes resulting in solid sodium oxalate and the evolution of hydrogen. The sodium oxalate is dissolved in water and causticized with hydrated lime to precipitate calcium oxalate, leaving a solution of sodium hydroxide which is concentrated somewhat and with makeup recycled in the process. The calcium oxalate is dumped into a large excess of dilute sulfuric acid at about 70° C to first precipitate calcium sulfate and then on cooling, oxalic acid dihydrate. To make ammonium oxalate from calcium oxalate directly, it is probably feasible to react ammonium sulfate with calcium oxalate, but this again necessitates sulfuric acid to make ammonium sulfate, further, the resulting hydrated calcium sulfate would probably represent a waste disposal problem.

Recently in a number of copending applications I have disclosed various processes for the production of sodium oxalate from essentially common salt and carbon monoxide from a blast furnace that should make the product economically. Thus in my copending application Ser. No. 497,040 filed Aug. 13, 1974 I show the coproduction of ammonium formate and a ferrous metal, the ammonium formate resulting from the hydrolysis of formamide which in turn is made from ammonia and carbon monoxide contained in the top gas from a blast furnace. This is emphasized to show that such carbon monoxide is obviously plentiful and cheap, meaning that ammonium formate can be cheap. In another copending application Ser. No. 433,296 filed Jan. 14, 1974 I disclose the addition of ammonium formate to a solution of common salt, NaCl, in liquid ammonia to precipitate rapidly pure anhydrous sodium formate. As it is well known in the art that sodium formate fuses at 400° C to sodium oxalate with the evolution of hydrogen, and further, to causticize sodium oxalate solutions with hydrated lime to precipitate calcium oxalate leaving a solution of caustic soda, it can be seen that as the caustic soda so produced is essentially the result of salt and lime, the overall process is a viable route to cheap caustic soda which obviates the use of electricity. But as calcium oxalate is a coproduct, uses for it must be found. Likewise in a copending application, Ser. No. 555,189 filed Mar. 4, 1975, I also disclose a process where limestone and sodium oxalate combine in water with the optional addition of carbon dioxide to also precipitate calcium oxalate, but leaving a solution of sodium carbonate or sodium bicarbonate. Here again, if the process is to be useful, new ways will need be found for processing calcium oxalate to other intermediates.

In British Pat. No. 477,230 and 517,455 it is shown that a slurry of calcium oxalate in a solution of certain metal salts, i.e., those of copper, and ammonium carbonate with an excess of ammonium hydroxide at 100° C and under pressure of several atmospheres, calcium carbonate precipitates, almost quantitatively. On examination of the solution it is found to contain the ammonia complex of the metal oxalate. This is fortuitous because the metal oxalate itself, for example copper oxalate, is insoluble. The other metal salts noted give oxalates which are usually insoluble, but those ammonia complexes are quite soluble.

A complete review of the literature of a Chemical Abstracts search does not show analogous technology. And indeed, if dry technical grade calcium oxalate such as is commercially available is slurried in an aqueous ammonium carbonate solution containing an excess of ammonium hydroxide and heated under pressure to 100° C, nothing happens. But it is now a very desirable end to find a process for the production of ammonium oxalate. Because it is known in the art to dehydrate ammonium oxalate to oxamide, a superior controlled release fertilizer. While heretofore the carbon monoxide route to oxalates was uneconomic with respect to the use of oxalates in the production of oxamide, by the various processes of my invention such oxalates which can be intermediates to oxamide are potentially cheap.

It should be noted that the literature is full of processes for the production of oxamide, practically all starting with cyanogen which is best made from hydrogen cyanide. It is ironic to note that hydrogen cyanide is made from natural gas, ammonia and oxygen via the androwsow process. But because of the natural gas shortage and other new factor, hydrogen cyanide is now best produced by the dehydration of formamide over alumina. As noted earlier, formamide is a starting material for making ammonium formate, sodium formate and then sodium oxalate.

Therefore, it is an object of my invention to provide and new and improved process for the production of ammonium oxalate.

My invention is a process for the production of ammonium oxalate wherein an oxalate of a metal whose carbonate is stable is combined with ammonium carbonate in water or oxygenated aliphatic media, or mixtures thereof, at a temperature in the range of from about −50° C to about 300° C.

I have discovered that calcium oxalate and ammonium carbonate in aqueous media at about 100° C yields a solution of ammonium oxalate, calcium carbonate being precipitated out. But the key to the process if there be one with respect to calcium oxalate is that freshly prepared calcium oxalate be used, it should not have undergone a high temperature drying process. Likewise with magnesium oxalate, but even magnesium oxalate which has been dried in ordinary drying ovens does participate in the process, but to a lesser conversion than freshly precipitated and undried magnesium oxalate. Ideally an excess of ammonium carbonate to metal oxalate, according to the stoichiometry,

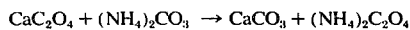

is used. And although the process can be conducted without added ammonium hydroxide, the more basic the process the more rapid and the more complete the conversion. A typical experiment is described in Example 1.

EXAMPLE 1

13 g calcium oxalate
15 g ammonium carbonate (50% excess)
100 ml. 40% ammonium hydroxide The agitated slurry was heated in a glass pressure reactor over an oil bath to a temperature for 2 hours at 100° C. On cooling and filtering it was found that the 10 g of solid residue contained about 90% calcium carbonate and the solution analyzed about 11 g ammonium oxalate.

Using these same proportions, a number of other metal oxalates were tried and found to operate in the process including those of magnesium, mixed calcium-magnesium, iron II, manganese II, nickel, copper I and II, cobalt and cadmium and zinc. But as the solubility of both the oxalates and carbonates of these metals is relatively low in water and ammonium hydroxide, it was decided to use methanol instead of water. The extent of conversion was found to be only slightly less. But of more interest was the fact that in this media under essentially the same conditions sodium and potassium oxalates gave ammonium oxalate and the respective solid carbonates. Again the rates and yields were lower than those of example 1.

Thus using either media or acetone, all oxalates of metals having stable carbonate could be so converted, but those of metals forming stable complexes with ammonia gave noticeably lower yields. While mixtures of water and methanol or acetone operate well in the process, only a few were tried. Likewise it was found that instead of ammonium carbonate, carbon dioxide could be added to the ammoniacal slurry with like results. Also ammonium carbonate can used in stead of ammonium carbonate. While it is difficult to exactly find the lower limit of ammonium ion concentration, it is preferred that the pH be greater than 9, ideally above 11. Likewise it is difficult to establish the ideal concentration of carbonate ion, ideally in the form of ammonium carbonate, required. But it is clear that a stoichiometric excess is desirable, ideally a large excess should be present.

Because ammonium oxalate is not very soluble at low temperatures, it is preferable to filter off the insoluble residue at higher temperatures, i.e., from about 40°–100° C after removing the excess ammonia, and then crystallize out ammonium oxalate at lower temperatures, ideally at or below 0° C. At 0° C the solubility of ammonium oxalate monohydrate in water is 2.5 parts per hundred. Using methanol as the media of the process a practically anhydrous ammonium oxalate can be obtained, but ammonium oxalate is not very soluble in methanol, even at somewhat higher temperatures.

As noted, ammonium oxalate is an intermediate to oxamide, a valuable controlled release fertilizer. Ammonium oxalate is also useful in the preparation of metal oxalates, for examples copper oxalate or nickel oxalate or manganous oxalate from extracts or their ores. Ferrous oxalate may be obtained by adding ammonium oxalate to hydrochloric acid pickle liquor, essentially ferrous chloride. Ferrous oxalate can be thermally decomposed in an atmosphere of hydrogen at about 450° to procude a pure iron powder. Both nickel and copper oxalates decompose in nitrogen or other inert gas at about 350° C to give the pure metals directly. Manganous oxalate is useful in the preparation of ferrites.

While most of the effect has been directed to the production of ammonium oxalate, it should be noted that the process yields simultaneously very finely divided carbonates, especially of calcium and magnesium which are excellent fillers for plastics. While there is always some unreacted metal oxalate in the carbonate, if the amount is considerable it can be removed by various chemical methods. For example, magnesium oxalate has considerable solubility in caustic soda while magnesium carbonate does not, providing a convenient separation process. Other oxalates have solubility in ammonium salts and in acids which can form the basis for a selective removal or extraction process.

As noted, in methanol or acetone, alkali metal oxalates simultaneously yield ammonium oxalate and sodium carbonate. This technology combined with the other processes noted earlier for the production of sodium oxalate from essentially salt and carbon monoxide offers the most direction route to both oxamide and soda ash or sodium bicarbonate, the precipitate is mostly soda ash, but some bicarbonate also appears to be present.

Whatever the metal carbonate, it is obvious that the process of my invention can be conducted continuously. One way simply to continuously add the metal oxalate and ammonium carbonate continuously to ammonium hydroxide in a pipe type reactor at a rate determined by the diameter and length of the pipe. Alternatively metal oxalate can be added continuously to the desired concentration of ammonium hydroxide with carbon dioxide being added continuously or intermittantly downstream. Many other variations are equally workable.

According to the patent statutes, I have explained the principle of my invention and have illustrated and described what I now consider to represent its best embodiment. However, I desire to have it understood that within the scope of the appended claims, the invention may be practiced otherwise than as specifically illustrated and described.

I claim:

1. A process for the production of ammonium oxalate and metal carbonates which are stable under the conditions of the process comprising reacting a metal oxalate with an adduct of carbon dioxide with ammonia or aqueous ammonium hydroxide in a liquid media selected from water, ammonia, methanol, acetone or mixtures thereof at temperatures in the range of −50° C to 300° C under conditions sufficient to retain the liquid media in the liquid state to form an ammonium oxalate and the corresponding metal carbonate.

2. The process of claim 1 wherein said carbon dioxide adduct with ammonia or ammonium hydroxide is formed in situ by adding carbon dioxide to said liquid media containing ammonia or ammonium hydroxide.

3. The process of claim 1 wherein said oxalate is calcium oxalate.

4. The process of claim 1 wherein said calcium oxalate is freshly prepared.

5. The process of claim 1 which is conducted continuously.

* * * * *